(12) United States Patent
Kundetkar

(10) Patent No.: US 11,998,365 B2
(45) Date of Patent: *Jun. 4, 2024

(54) SYSTEM AND METHOD FOR DIAGNOSTIC ANALYSIS OF HUMAN BODY SYSTEMS, ORGANS, AND CELLS

(71) Applicant: KMZ Holdings LLC, New York, NY (US)

(72) Inventor: Nandan Kundetkar, Mumbai (IN)

(73) Assignee: KMZ Holdings, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/465,674

(22) Filed: Sep. 2, 2021

(65) Prior Publication Data

US 2021/0393213 A1 Dec. 23, 2021

Related U.S. Application Data

(63) Continuation of application No. 16/536,074, filed on Aug. 8, 2019, now Pat. No. 11,134,900.

(30) Foreign Application Priority Data

Jul. 23, 2019 (IN) .............................. 201911029722

(51) Int. Cl.
| | | |
|---|---|---|
| *A61B 5/00* | (2006.01) | |
| *A61B 5/055* | (2006.01) | |
| *G16H 10/60* | (2018.01) | |
| *G16H 50/20* | (2018.01) | |
| *A61B 5/021* | (2006.01) | |

(52) U.S. Cl.
CPC ............ *A61B 5/7275* (2013.01); *A61B 5/055* (2013.01); *A61B 5/7257* (2013.01); *G16H 50/20* (2018.01);
(Continued)

(58) Field of Classification Search
CPC ..... A61B 5/7275; A61B 5/055; A61B 5/7257; A61B 5/7246; A61B 5/02108;
(Continued)

(56) References Cited

U.S. PATENT DOCUMENTS 8,512,240 B1 8/2013 Zuckerman-Stark et al.
9,442,065 B2 9/2016 Gulati et al.
(Continued)

FOREIGN PATENT DOCUMENTS

KR 10-2014-0081095 A 7/2014
KR 10-2018-0079757 A 7/2018
(Continued)

OTHER PUBLICATIONS

"Encyclopaedia Britannica, Dielectric, Dec. 16, 2011, Encyclopaedia Britannica, Inc., Science" (Year: 2011).
(Continued)

*Primary Examiner* — Joseph M Dietrich
*Assistant Examiner* — Michael T. Holtzclaw
(74) *Attorney, Agent, or Firm* — Womble Bond Dickinson (US) LLP

(57) ABSTRACT

A system and method for providing diagnostic analysis of a physical condition of a human body. A signal generator, an emitter, a receiver, and processor(s) generate a baseline signal. In some implementations, the emitter may emit the baseline signal through cells of the human body over scanning points for a predetermined amount of time, and a receiver detects reflected signals that have propagated through the cells of the human body. Some implementations include determining, by the one or more processors, a power spectrum density (PSD) of the reflected baseline signal and a spectral variance in the PSD of the reflected baseline signal relative to the baseline signal. Some implementations may compare the spectral variance to one or more predetermined
(Continued)

spectral variances corresponding to one or more conditions of the human body and determine the condition of the human body, based on the comparison.

24 Claims, 6 Drawing Sheets

(52) U.S. Cl.
CPC ......... *A61B 5/02108* (2013.01); *A61B 5/7203* (2013.01); *A61B 5/7246* (2013.01); *A61B 5/725* (2013.01); *G16H 10/60* (2018.01)

(58) Field of Classification Search
CPC ...... A61B 5/7203; A61B 5/725; G16H 50/20; G16H 10/60
See application file for complete search history.

(56) References Cited

U.S. PATENT DOCUMENTS

| | | |
|---|---|---|
| 2004/0100376 A1 | 5/2004 | Lye et al. |
| 2010/0130873 A1 | 5/2010 | Yuen et al. |
| 2010/0152600 A1 | 6/2010 | Droitcour et al. |
| 2012/0245481 A1 | 9/2012 | Blanco et al. |
| 2015/0164375 A1 | 6/2015 | Schindhelm et al. |
| 2017/0128019 A1 | 5/2017 | Shao et al. |
| 2018/0368739 A1 | 12/2018 | Zhang et al. |
| 2019/0298177 A1 | 10/2019 | Moon et al. |
| 2019/0336038 A1 | 11/2019 | Gorgutsa et al. |
| 2020/0300972 A1 | 9/2020 | Wang et al. |

FOREIGN PATENT DOCUMENTS

| | | |
|---|---|---|
| WO | WO2018050913 | 3/2018 |
| WO | WO2019122413 | 6/2019 |

OTHER PUBLICATIONS

Ntemational Search Report & Written Opinion for Related Application PCT/US2019/047938, dated Apr. 23, 2020, pp. 1 to 10.
Canadian Office Action for App. No. 3,148,525, dated Sep. 28, 2023, 3 pgs.
European Supplemental Search Report for App. No. 19938266.4, dated Jul. 10, 2023, 10 pgs.

SYSTEM AND METHOD FOR DIAGNOSTIC ANALYSIS OF HUMAN BODY SYSTEMS, ORGANS, AND CELLS

CROSS-REFERENCE TO RELATED APPLICATIONS

This patent application is a continuation of U.S. patent application Ser. No. 16/536,074, filed Aug. 8, 2019, entitled "SYSTEM AND METHOD FOR DIAGNOSTIC ANALYSIS OF HUMAN BODY SYSTEMS, ORGANS, AND CELLS", which claims the benefit of Indian Patent Application No. 201911029722 filed on Jul. 23, 2019, entitled "SYSTEM AND METHOD FOR DIAGNOSTIC ANALYSIS OF HUMAN BODY SYSTEMS, ORGANS, AND CELLS, naming as inventor Nandan KUNDETKAR, which is incorporated by reference.

BACKGROUND

Field

The present disclosure pertains to a system and method for diagnostic analysis of human body systems, organs, and cells.

Description of the Related Art

Diagnostic testing systems for diagnostic analysis of human body systems, organs, and cells are known. Diagnostic testing methods utilizing various methodologies ranging from bodily fluid collection in various formats and volumes, bodily electrical activity (e.g., EMG and ECG), static and dynamic imaging (e.g., MRI and Doppler ultrasound) are also known. However, previous solutions are time-consuming, costly, and invasive to the patient.

SUMMARY

Accordingly, one or more aspects of the present disclosure relate to a system for providing diagnostic analysis for a physical condition of the human body. In some implementations the system may include a signal generator, an emitter, a receiver, and one or more processors in communication with a memory having non-transitory computer readable instructions stored thereon that when executed by the one or more processors cause the system to generate, by the signal generator, a baseline signal. In some implementations the system emits, utilizing the emitter, the baseline signal through one or more cells of the human body over a plurality of scanning points for a predetermined amount of time. In some implementations, the system may receive, by the receiver, one or more reflected signals that have propagated through the one or more cells of the human body and determine, by the one or more processors, a power spectrum density (PSD) of the reflected baseline signal. In some implementations, the system may determine, by the one or more processors, a spectral variance in the PSD of the reflected baseline signal relative to the baseline signal and compare, by the one or more processors, the spectral variance to one or more predetermined spectral variances corresponding to one or more physical conditions of the human body. In some implementations, the system may determine, by the one or more processors, the condition of the human body, based on the comparison and transmit a report indicating the condition of the human body to a clinician, and/or other users.

Some implementations relate to a method for providing diagnostic analysis for a physical condition of the human body utilizing a system. In some implementations, the system may include a signal generator, an emitter, a receiver, and one or more processors in communication with a memory having non-transitory computer readable instructions stored thereon. In some implementations, the one or more processors execute the non-transitory computer readable instructions and cause the system to execute the method. In some implementations, the method includes generating, by the signal generator, a baseline signal. In some implementations, the method includes emitting, utilizing the emitter, the baseline signal through one or more cells of the human body over a plurality of scanning points for a predetermined amount of time. In some implementations, the method may include receiving, by the receiver, one or more reflected signals that have propagated through the one or more cells of the human body and determining, by the one or more processors, a power spectrum density (PSD) of the reflected baseline signal. In some implementations, the method may include determining, by the one or more processors, a spectral variance in the PSD of the reflected baseline signal relative to the baseline signal and comparing, by the one or more processors, the spectral variance to one or more predetermined spectral variances corresponding to one or more physical conditions of the human body. In some implementations, the method may determine, by the one or more processors, the physical condition of the human body, based on the comparison and transmit a report indicating the condition of the human body to a clinician and/or other users.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY IMPLEMENTATIONS

Figure 1:
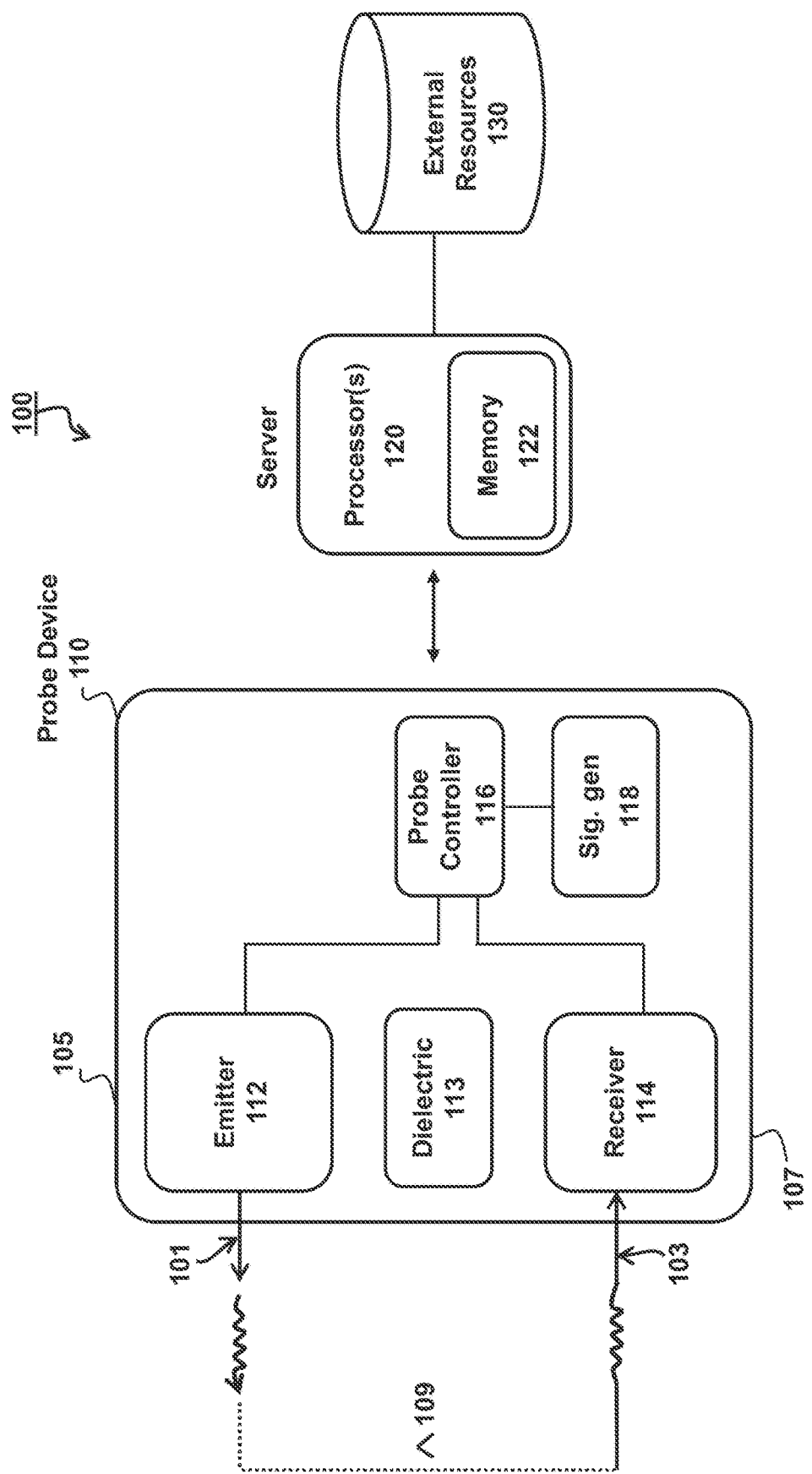
FIG. 1 is a schematic representation of a system for diagnostic analysis in accordance with one or more implementations.

The present invention will now be described in detail with reference to the drawings, which are provided as illustrative examples of the invention so as to enable those skilled in the art to practice the invention. Notably, the figures and examples below are not meant to limit the scope of the present invention to a single implementation, but other implementations are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. As used herein, the singular form of "a", "an", and "the" include plural references unless the context clearly dictates otherwise. As used herein, the statement that two or more parts or components are "coupled" shall mean that the parts are joined or operate together either directly or indirectly (i.e., through one or more intermediate parts or components, so long as a link occurs).

Implementations described as being implemented in hardware should not be limited thereto, but can include implementations implemented in software, or combinations of software and hardware, and vice-versa, as will be apparent to those skilled in the art, unless otherwise specified herein. In the exemplary implementations described herein, an implementation showing a singular component should not be considered limiting; rather, the invention is intended to encompass other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

As used herein, "directly coupled" means that two elements are directly in contact with each other. As used herein, "fixedly coupled" or "fixed" means that two components are coupled so as to move as one while maintaining a constant orientation relative to each other. As used herein, "operatively coupled" means that two elements are coupled in such a way that the two elements function together. It is to be understood that two elements "operatively coupled" does not require a direct connection or a permanent connection between them.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality). Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The human body and constituent systems, organs, and cells, from a diagnostic perspective, are currently quantified and qualified in a number of different ways. Qualitative and quantitative measurement is done both to determine variances or stasis of determined values. If a deterioration from the established values of norms occurs (e.g., deviation of glucose from an average norm of 5.5 mmol/L) speculation occurs with a hybrid of both symptom analysis and further testing, which often leads to more speculation and repetition of this same cycle. This is inefficient with time, costly, and invasive to the patient.

Current testing modalities are time consuming, invasive, and present discomfort to the patient. One or more embodiments described herein provide diagnostic testing with zero administration of any substance to the patient and without requiring any sample collection from the patient. For example, in some tests the patient is required to have pre-exposure to some fluids either consumed orally intravenously. Results are obtained as color values rather to be interpreted for an abnormality instead of identifying specifically the abnormality. In displays the colors are in the combination of R-G-B or Y-U-V the same in non-display form can be based on the numeric value on a logarithmic scale based on a multibit form of the color values. Note that even before the display which comes on the screen which is a static image or variable image is derived out of multibit resolution coming at some output level. Mainly any input to output level time to time will vary based on the treatment results to come in due course. For example, any particular abnormality inputs and outputs are never changed nor its processing in between. What changes is that at some level instead of one abnormality a few more or found which would be derived by finding more steps in the resolutions, in time to come to grasp the same and find more values in processing and giving results at the output.

One or more embodiments include input, processing, and output parameters, which are so well controlled that defining any variation with abnormalities would not require any interphase system change or the input probe device. For example, while one may be examining an abnormality in the liver the effects could also be seen in the pancreas. Immediately the input has the provision to enhance inputs by virtue of resolution change and same would be at process and output level. What will change is probably the degree of severity or another abnormality or disease condition if there are two distinct identifiable abnormalities within the same system or outside of the same system due to systemic interaction of the whole body. For example, the system may include cardiac and endocrine systems.

While previous diagnostic methodology includes speculative testing and speculation about symptoms, one or more implementations describe herein provide a diagnostic analysis system and method that dramatically increase diagnostic analysis capabilities in terms of time, immediate collaboration with other specialists, and is non-invasive to the human body (i.e., zero bodily fluid collection including blood, and/or no need to perform other invasive procedures). Some implementations described herein facilitate instant collaboration anywhere in the world with any specialist with real time results right in the doctor's office. As discussed in detail below, some implementations may implement a bottom up approach at the most consequential level (e.g. cellular, DNA and RNA analysis) for diagnostic analysis utilizing a diagnostic probe device the size of magic marker (as one non-limiting example) interfacing with a diagnostic analysis server that is web based and thus can be utilized computers across the world.

Referring now to FIG. 1, FIG. 1 depicts an exemplary diagnostic analysis system 100 in accordance with one or more implementations. Diagnostic analysis system 100 may include probe device 110 in communication with web-based server processors 120, and external resources and/or electronic storage 130. As shown in FIG. 1, probe device 110 may, in some implementations, include emitter 112, dielectric 113, receiver 114, and probe controller 116. Emitter 112 may emit a baseline signal 101. For example, signal generator 118 may generate baseline signal 101, which is communicated to emitter 112 for transmission into the cells of the human body, which is discussed in further detail below. Receiver 114 may detect a reflected signal 103 and communicate signal 103 to probe controller 116 which may then relay the signal 103 to server processors 120.

In some implementations, probe controller 116 may be in communication with signal generator 118 and includes one or more hardware processors (not shown in FIG. 1) and/or field and/or programmable gate arrays (FPGA) that execute non-transitory machine-readable instruction in order to carry out the exemplary implementations described herein. In some implementations, non-transitory machine-readable instructions may be hardcoded in probe controller 116 and/or server processors 120 (e.g., Firmware, BIOS, Bootstrap, and the like).

As shown in FIG. 1, server processor 120 may be in communication with server memory 122. Server memory 122 may store non-transitory machine-readable instructions that when executed by server processors 120 carry out the exemplary implementations described herein. In some implementations, server processors 120 are in wireless communication to probe device 110. Communication between probe device 110 and server processors 120 may be, in some implementations, facilitated by a wireless network (not shown), which may be implemented via a WAN/LAN network that is connected to the Internet via a hybrid fiber-optic cable (HFC) communication network provided by an Internet Service Provider (ISP). In some implementations, communication between probe device 110 and server processors 120 may be implemented via a wireless communication utilizing NFC, BLUETOOTH, BLE, GSM, TDMA, CDMA, 3G, 4G, LTE, 5G, or any other wireless communication protocol capable of establishing wireless communication. In some implementations, server processors 120 may be configured as one or more blade servers in server rack as part of a data center or information handling system. In some implementations, the functionality of server processors 120 is provided by processing components (e.g., processing circuitry of controller 116) of probe device 110, and/or other components of the present system.

In some implementations, probe controller 116 and/or server memory 122 may comprise electronic storage media that electronically stores information. The electronic storage media of probe controller 116 and/or server memory 122 may comprise one or both of system storage that is provided integrally (i.e., substantially non-removable) with probe device 110 and/or removable storage that is removably connectable server processors 120, for example, a port (e.g., a USB port, a firewire port, etc.) or a drive (e.g., a disk drive, etc.). Controller 116 server memory 122 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Controller 116 and/or server memory 122 may store software algorithms, information determined by processors 120, information received receiver 114 and/or external computing systems (not shown), and/or other information that enables system 100 to function as described herein External resources and/or electronic storage 130 may include one or more empirical databases (not shown). Empirical databases of electronic storage 130 may include predetermined and spectral variances and power spectral density corresponding to known conditions of the human body relative to individual cells, which is discussed in further detail below. In some implementations, electronic storage 130 comprises electronic storage media that electronically stores information (e.g. empirical databases). The electronic storage media of electronic storage 130 may comprise one or both of system storage that is provided integrally (i.e., substantially non-removable) with system 100, 500 and/or removable storage that is removably connectable to system 100, 500 via, for example, a port (e.g., a USB port, a firewire port, etc.) or a drive (e.g., a disk drive, etc.). Electronic storage 130 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), cloud storage, and/or other electronically readable storage media. Electronic storage 130 may store software algorithms, information determined by processor(s)120 and/or controller 316, information received via probe device 110 and/or other computing systems, and/or other information that enables system 100, 500 to function as described herein. Electronic storage 130 may be (in whole or in part) a separate component within system 100, 500, or electronic storage 130 may be provided (in whole or in part) integrally with one or more other components of system 100, 500 (e.g., server processors 120).

In some implementations, probe device 110 may comprise a wireless handheld device. In some embodiments, probe device 110 may be worn by a user and/or have other forms (e.g., the form of probe device 110 is not intended to be limiting). In some implementations, probe device 110 may be dipolar in nature and emit an electromagnetic field facilitated by baseline signal 101. For example, emitter 112 and receiver 114 may be separated by dielectric 113. Dielectric 113 serves to separate sending and receiving electromagnetic functionality of probe device 110 (e.g. emitter 112 and receiver 114). Doing so increases the accuracy of detected signals and thus increases the accuracy of determinations of physical conditions of the human body, as discussed in further detail below. Dielectric 113 may be and/or include any material that allows probe device 110 to function as described herein.

In some implementations, probe device 110 may be hard coded with a PLL patch, which is discussed in further detail below. Probe controller 116 and or signal generator 118 may comprise a system-on-a-chip (SoC) microcontroller having a size of 1 cm×1.5 cm×2 cm, for example. In some implementations, probe device 110 may be a wireless handheld device that may be 15 cm in length and 5 cm circumference. In some embodiments, probe device 110 may be configured as a bracelet. In some embodiments, probe device 110 may have other form factors. The form factor of probe device 110 is not intended to be limiting. In some implementations, probe device 110 may include emitter 112 and receiver 114 separated by dielectric 113.

As discussed in further detail below, probe device 110 may collect data used for human body condition determinations, which may be facilitated by scanning probe device 110 over a human body. The human body conditions may include medical ailments, injuries, diseases, infections, sicknesses, vital signs, and/or other conditions. In some implementations, the total time for data collection by the probe device 110 may be about 100 seconds as one non-limiting example. Probe device 110 may in this manner detect a reflected signal 103 that is received by receiver 114 and transmitted for diagnostic analysis to server processors 120. Diagnostic analysis performed by server processors 120 (and/or other more local computing devices operatively coupled to probe device 110) may include determining results pertaining to one or more physical conditions of the human body. In some implementations, server processors 120 (and/or a local computing device) may include a multi-algorithmic, web based, software system that issues results in up to 90 seconds, for example (this length of time is not intended to be limiting). In some implementations processors 120 may issue results (e.g., human body condition determinations) and less than 90 seconds, or more than 90 seconds.

Diagnostic analysis system 100 may generate an electromagnetic signal and field that propagates through the cells of the human body. And in doing so, transmit a reflected wave which backpropagates in the direction of an incident angle to the reflected medium, which is discussed in further detail below. In some implementations, probe device 110 may continuously scan for a predetermined amount of time and collect a predetermined number of (e.g., at least 2 billion) data points. For example, in one implementation, probe device 110 may scan for no more than 100 seconds. In doing so, probe device 110 facilitates data collection of billions of data points.

In some implementations, data collected from scanning points (e.g., locations) over the human body may include eV data. This eV data may include magnetic field perturbations corresponding to reflected signal 103. Scanning points (e.g., the locations where the scanning occurred) and corresponding eV data are sent to server processors 120 where a database of normal eV values is measured against data collected from the patient. In some implementations, the database may be housed by electronic resources 130

For example, each and every human cell or any organism has a voltage potential across its body. Similarly, any cell has a potential difference denoted by an eV value. When eV value corresponding the cell's voltage potential value remains unchanged, the particular. When a large number of the cell values are going low, a pattern may be identified in terms of the cell values coming from the region. The region can easily be determined when the data corresponds to the RNA position. From there system 100 can analyze any hierarchy up or down (e.g. cell to organ to system and vice versa). Thus, when human cells and their eV value found in amplitude is are as expected, this finding corresponds to a determination that the cell organ is good. Because the eV of a cell is a small parameter, to increase accuracy, in some embodiments, system 100 may compare input/output signal 101/103 at the level of the Phase Difference and include calculations based on amplitude and phase.

In some implementations, signal generator 118 may generate baseline signal 101. Baseline signal 101 may include data input sent in the frequency domain. In some implementations, baseline signal 101 may be emitted such that for every time unit, T1, a resolution of time is used as a stream of data sent in the time domain (e.g., T1) and compared to the same on its reverse path (i.e., reflected signal 103 is compared to baseline signal 101) based on characteristics of the portion of the human body being measured, which is described in further detail below. In some implementations, any noise and/or error may be considered by convolving the time domain signal back to the frequency domain and reemitting baseline signal 101, as discussed above. In some implementations, probe controller 116 and signal generator 118 may detect delay based on biological conditions of the human body and drop in signal levels. Both may be converted and compared on Phase Level as a Schrodinger Equation on the footprint of a Fourier Transform.

In some implementations, server processors 120 implement a phase comparison as discussed above with probe device 110, held by a patient merely acting as an emitter and a sensor (e.g., emitter 112, receiver 114). For example, baseline signal 101 may be emitted from a first side 105 of probe device 110 and received at a second side 107 proximate to first side 105. The return path 109, where baseline signal 101 propagates through cells of the human body provides the different structure measurements in the reflected signal 103, which are on a phase scale as an angle of measurement on a Radian scale, which is discussed in further detail below.

Figure 2:
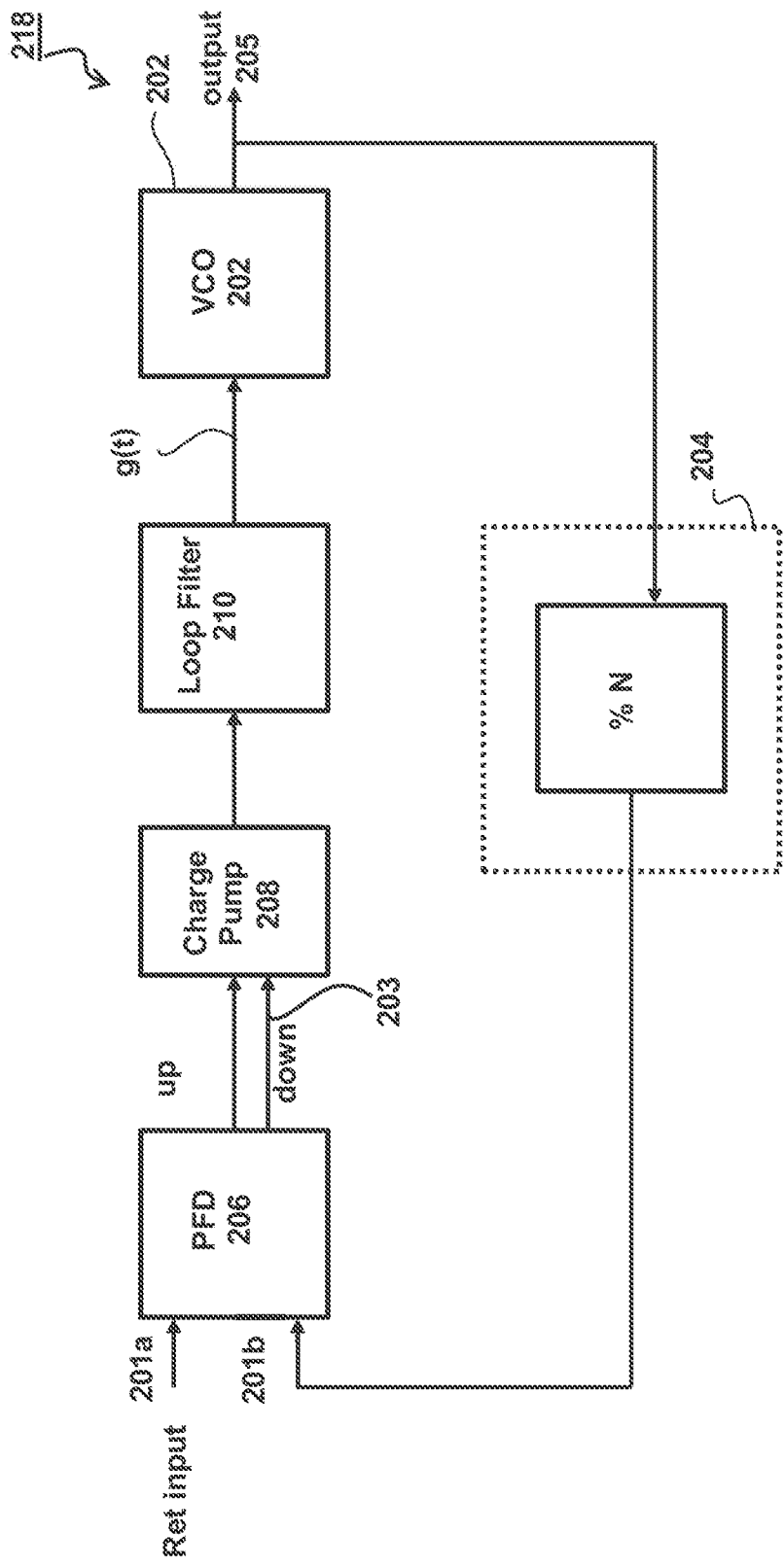
FIG. 2 is a schematic representation of an exemplary signal generator used for a diagnostic analysis in accordance with one or more implementations.

Referring now to FIG. 2, FIG. 2 depicts an exemplary phase locked loop (PLL) signal generator fashioned as a feedback control system. PLL 218 may include voltage-controlled oscillator (VCO) 202, frequency divider 204, phase frequency detector (PFD) 206, charge pump 208, and filter 210. In some implementations, VCO 202 may include one or more crystal oscillators, an LC circuit, a tank circuit, or other hardware and/or software configured to generate a frequency modulated signal. In some implementations, PLL signal generator 218 may utilize one or more additional frequency multipliers, adders, dividers, multiplexers, demux, data registers, and the like (not shown).

In some implementations, PLL 218 may function to compare the phases of two input signals (e.g., inputs 201*a* and 201*b* of PFD 206) and generates an error signal (e.g., output 203) that is proportional to the difference between phases of the input signals. The error signal (i.e., output of PFD 206) is then amplified via charge pump 208 and filtered utilizing loop filter 210. The filtered output signal, g(t), is then used to drive VCO 202, which generates an output frequency 205. The output frequency is then sent to frequency divider 204 and back to input 201*b* of PFD 206, thus producing a negative feedback loop as shown in FIG. 2.

In some implementations, phase frequency detector 206 may compare the phase at each input 201*a* and 201*b* and generate an error signal φ(t), which is proportional to the phase difference between the two inputs 201*a* and 201*b*. Since the two inputs 201 are at the same frequency when the loop is locked, one output at twice the input frequency and an output proportional to the cosine of the phase difference. The doubled frequency component may be removed by a lowpass loop filter 210, for example. Any phase difference then shows up as the control voltage to the VCO, which may include a DC or slowly varying AC signal after filtering. Phase difference shows up when the output frequency 203 drifts, the phase error signal, output 203, will increase, driving the frequency of the signal in the opposite direction so as to reduce the phase error. Thus output 205 is locked to the frequency at the input 201. Input 201*a* may include a reference signal (e.g. REF input) and is usually derived from a crystal oscillator (not shown), which is very stable in frequency.

The key to the ability of a frequency synthesizer to generate multiple frequencies is the divider 204 placed between the output and the feedback input. This may be in the form of a digital counter (e.g., counter 330 infra), with the output signal acting as a clock signal. The counter is preset to some initial count value and counts down at each cycle of the clock signal. When it reaches zero, the counter output changes state and the count value is reloaded. PLL 218, because it is digital in nature, is very easy to interface to other digital components or a microprocessor (e.g. 116).

This allows the frequency output by the synthesizer to be easily controlled by a digital system.

In some implementations, an exemplary PLL signal generator 218 may operate in accordance with the below description illustrating equations governing a phase locked loop with an analog multiplier as the phase detector and linear filter. For example, in some implementations, input signal 201 may be described as:

$$f1(\theta1(t))f1(\theta1(t)),$$

and the output signal 203 at VCO 202 may be described as $$f2(\theta2(t))/f2(\theta2(t))$$

with phase $$\theta1(t),\theta2(t)).$$

The functions $$f1(\theta),f2(\theta)$$

may describe waveforms of signals (e.g., baseline signal 101). In some implementations, PFD output signal 203 of phase detector 206 may be given by $$\phi(t)=f1(\theta1(t))f2(\theta2(t)),$$

wherein $$g(v)$$

is the sensitivity of VCO 202 and may be expressed in Hz/V ω, where ω is a free running frequency of VCO 202. For example, in some implementations VCO 202 may output frequency ω at 14 GHz, or more. [41] In some implementations, loop filter 210 may provide filtering the signal output by charge pump 202. Charge pump 202 may function to amplify the signal output by PFD 206 in order to provide signal conditioning functionality for accurate signal detection. In some implementations, loop filter 210 may operate in accordance with the following system of linear differential equations:

$$\dot{x}=Ax+b\phi(t),g(t).$$

$$g(t)=c^*x$$

In some implementations, $\phi(t)$ may be an input of loop filter 210 and represents an initial state of the filter. The star symbol above represents a conjugate transpose, wherein:

$$A=n-b(y)\text{-matrix},x\in \mathbb{C}^n, b\in \mathbb{R}^n, c\in \mathbb{C}^n, \ldots, x0\in \mathbb{C}^n.$$

Accordingly, in some implementations, the following system may describe the transfer function of the PLL signal generator 210: For example, VCO 202 may oscillate at an angular frequency, $\omega_{out}$ $$\dot{x}=Ax+bf1(\theta1(t))f2(\theta2(t)),$$

$$\dot{\theta}2=\omega\text{free}+gv(c^*x)$$

wherein θ0 is an initial phase shift.

In some implementations, the conjugate transpose may correspond to a Fourier transform of a Gaussian function $$f(x)=e^{-ax^2}$$

may be described by the below equations:

$$\mathcal{F}_x[e^{-ax^2}](k) = \int_{-\infty}^{\infty} e^{-ax^2} e^{2\pi ikx}dx$$

$$\int_{-\infty}^{\infty} e^{-ax^2}[\cos(2\pi kx) - i\sin(2\pi kx)]dx =$$

$$=\int_{-\infty}^{\infty} e^{-ax^2}\cos(2\pi kx)\,dx - i\int_{-\infty}^{\infty}e^{-ax^2}\sin(2\pi kx)dx.$$

As the second integrand is odd, therefore integration over a symmetrical range gives 0. Thus:

$$\mathcal{F}_x[e^{-ax^2}](k) = \sqrt{\frac{\pi}{a}} e^{-\pi^2 k^2/a},$$

Figure 3:
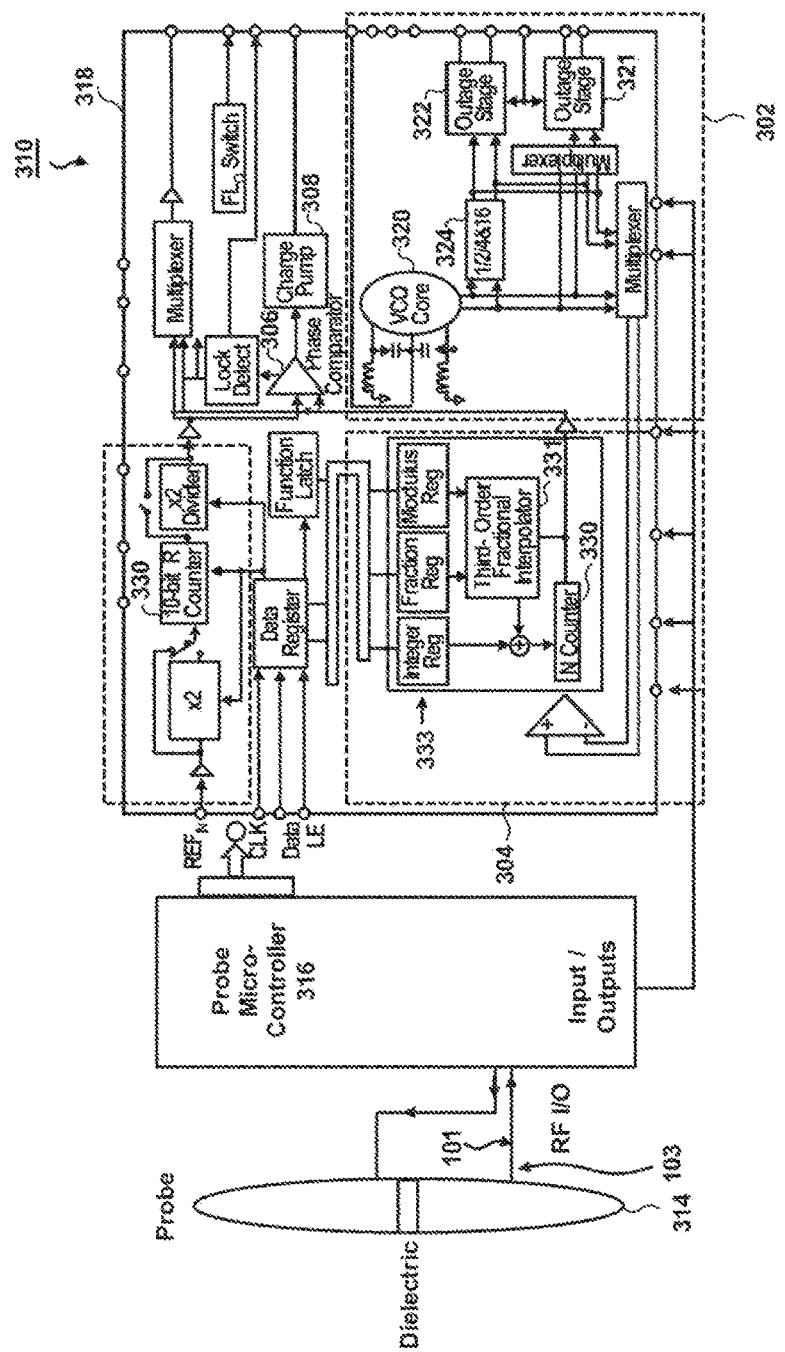
FIG. 3 is a schematic representation of exemplary circuitry for a diagnostic analysis probe device in accordance with one or more implementations.

As described in further detail below, in some implementations, the PLL 203 output is compared against a baseline database of normal values in order to determine a physical condition of the human body. Referring now to FIG. 3, FIG. 3 depicts an exemplary diagnostic analysis probe 310 in accordance with some implementations. Probe 310 is an exemplary implementation of probe device 110, of FIG. 1, in which similarly labeled parts and numbers correspond to similar functionality. As shown in FIG. 3, probe 310 includes VCO 302, PFD 306, charge pump 308, frequency divider 304 and loop filter 310 signal generator. In some implementations signal generator 318 may include a dual PLL signal generator 318 having an operating range of at least 14 GHz. PLL 318 generates baseline signal 101.

In some implementations, PLL also generates an identifier, wherein the baseline signal comprises a first carrier signal corresponding to a primary baseline signal and a second carrier signal corresponding to the identifier. Signal generator 318 may utilize a combination of time division multiple access (TDMA) and/or orthogonal frequency division multiple access (OFDMA) in order transmit first and second carrier signals as baseline signal 101.

For example, VCO core 320 may receive a reference signal as input (e.g., REF(in)) and may output a first carrier signal corresponding to baseline signal 101 via output stage 321 and may generate a second carrier signal corresponding to an identifier, via output stage 322. In some implementations the second carrier signal may undergo frequency shift keying phase shift keying in order to distinguish the identifier signal. As shown in FIG. 3, the first carrier signal and the second carrier signal output by output stage 322, 321 respectively, may be multiplexed into a single output signal 101. Multiplexing may be accomplished utilizing TDMA and/or OFDMA protocols. In some implementations, signal generator 318 may utilize tiers of frequency multipliers operating at very high frequency values which come in the category of electromagnetic fields which are in the range of 14 GHz and above (e.g., frequency divider 304).

In some implementations, frequency divider 304 may be placed between the output and the feedback input. This may be implemented utilizing a digital counter 330, with the output signal acting as a clock signal. For example, counter 330 may be preset to an initial count value and counts down at each cycle of the clock signal (CLK). When counter 330 reaches zero, counter 330 output changes state and the count value is reloaded. In some implementations, one or more flip-flops and/or data registers may complement frequency multiplying and signal division functionality as shown in FIG. 3. Doing so allows for the ability to easily interface to other digital components and/or microprocessors. Moreover, the frequency output by signal generator 318 may be controlled by digital systems (e.g. system 100).

In some implementations, frequency divider 304 may include a third order fractional interpolated 331 for implementing a fractional-N(frac-N) PLL synthesizer utilizing one or more fractional, integer, and/or modulus registers 333. Utilizing a frac-N PLL facilitates higher reference frequency values REF in, which results in a smaller multiplier term N. Also, utilizing a frac-N divider allows step sizes on the order of tens of Hertz. The frac-N also will lock faster when compared to a similar integer-N PLLs due to the lower value of N, which allows a wider loop filter bandwidth, which in turn allows a faster lock time. In some implementations, an SDH (Synchronous Digital Hierarchy) generator using a dual PLL is used to generate the signal.

As discussed in further detail below, one or more implementations described herein implement the sending of the baseline signal 101 through the cells of the human body and retrieving reflected signal 103. In some implementations, probe device 310 may detect and observe the difference in the baseline signal 101 that is sent versus reflected signal 103. For example, receiver 314 may be able to detect magnetic field perturbations corresponding to at least a portion of the reflected signal 103 in an order of magnitude corresponding to one Nano Gauss or smaller. In some implementations, the observed difference between signals 101, 103 is compared to a baseline database of existing normal signals and signal ranges, which is discussed in further detail below.

In some implementations, signals 101/103 is compared with the type of modulation resulting from propagating the input signal through cells of the human body. The modulation comparison may include determining and analyzing a differential generated out of the phase. In some embodiments, distortion is removed from the modulation comparison. For example, when the distortion is coming multiple times, the mean of the signal is taken, the wave is shifted, and the phases are actually compared. Each normal signal will depend always based on there a signal that is identified and earmarked so it is possible to determine while sending what is the signal and what is the return output (e.g., signal 101/103). The return output of each modulated signal including the amplitude of that variation is calculated by shifting the return signal and by calculating Phase.

As discussed above, in some implementations, at FSK/PSK block 324 an identifier signal may be implemented by utilizing frequency shift key (FSK) or phase shift Key (PSK) signal modulation techniques. For example, FSK may implement frequency modulation that assigns bit values to discrete frequency levels of baseline signal 101. In some embodiments, FSK may be divided into noncoherent or coherent forms. In noncoherent forms of FSK, the instantaneous frequency shifts between two discrete values termed the "mark" and "space" frequencies. In coherent forms of FSK, there is no phase discontinuity in the output signal. FSK modulation formats generate modulated waveforms that are strictly real values. In contrast, PSK in a digital transmission refers to a type of angle modulation in which the phase of baseline signal 101 for example, is discretely varied, in relation to a reference phase or to the phase of the immediately preceding signal element. This is done in order to represent data being transmitted. For example, in some implementations, when encoding bits, an exemplary PSK phase shift of baseline signal 101 could be 0 degree for encoding a "0," and 180 degrees for encoding a "1," or the phase shift could be −90 degrees for "0" and +90 degrees for a "1," thus making the representations for "0" and "1" a total of 180 degrees apart.

In some implementations, PSK may be implemented at block 324 so that the carrier signal may assume only two different phase angles, each change of phase carries one bit of information, that is, the bit rate equals the modulation rate. When the number of recognizable phase angles is increased to four, then 2 bits of information can be encoded into each signal element; likewise, eight phase angles can encode 3 bits in each signal element, for example. Thus, by implementing FSK, PSK 324 at different frequencies, baseline signal 101 and corresponding identifier may include varying different number of frequencies.

Accordingly, in some implementation, signal generator 318 may include a dual signal PLL which may emit a baseline signal and the identifier, which is an FSK and/or PSK of the baseline signal. The identifier (not shown) may be an FSK and/or PSK modulated baseline signal 101. Thus, baseline signal 101 and corresponding identifier may include thousands of different combinations and FSK, PSK can have combinations of multiple frequency. These values are compared against a baseline database of normal data points that have been acquired from intense empirical research and stored in external resources 130, for example.

In some implementations, diagnostic analysis system 100 (FIG. 1), in accordance with one or more implementations described herein employs a hierarchical paradigm going from body, to systems, to organs, to cells of the human body. Each frequency itself has an identifier (e.g. FSK/PSK of baseline signal 101), which may correlate to different organs within different systems. In some implementations, the signal processing is divided based on the resolution through which the signals (e.g., 101/103) are passed.

For example, in some embodiments, input signal 101 may include 3 input signals combined into a single carrier signal. System 100 identifies abnormalities and those issues are defined at the cellular level and/or system level. When system 100 identifies issues in a particular organ or systemic issues, system 100 may render interactivity across organs intra and inter systemically. For example, system 100 identifies cellular issues and also issues within a given process (i.e., extrapolating upward from the cellular level). For example, when there may be issues with cardiac and neurology systems or kidney and bladder at the organ level, or various combinations at different levels.

Once all the parameters are available a user of system 100 may decide how best to project the parameters. For example, when there is a blockage at the same time the liver has functionality issues that affects the blood pressure, the data can be viewed by various specialists. Based on the aggregate of the data the decision may be simply to remove the blockage. However, this may ignore the etiology of the blockage so another specialist may want to address the problem. With this 360 degree approach etiology instead of just the manifestation of that etiology can be determined and potentially treated. Thus, system 100 provides for a truly collaborative approach across multiple specialties.

Meaning each signal is identified by an identification (a combination of FSK over PSK and the frequency). Ibis creates not only enough number of processes for analysis its nature keeps enough room for any further certain development for a deeper analysis whose variable data is derived out of the interpolation of the frequency combination of FSK over PSK and the frequency.

In some implementations, microcontroller 316 has dual PLL 318 hard coded into the microcontroller 316 (e.g., as BIOS, Firmware, and/or software stored on memory, not shown). In some implementations, dual PLL 318 also contains the Fourier Transform hard coded, as discussed above. In some implementations, diagnostic analysis system 100 obtains logarithmic data (e.g., utilizing server processors 120) of increasing or decreasing frequency from the output from a directory of coded references (baseline or norm data for all data points.

Figure 4:
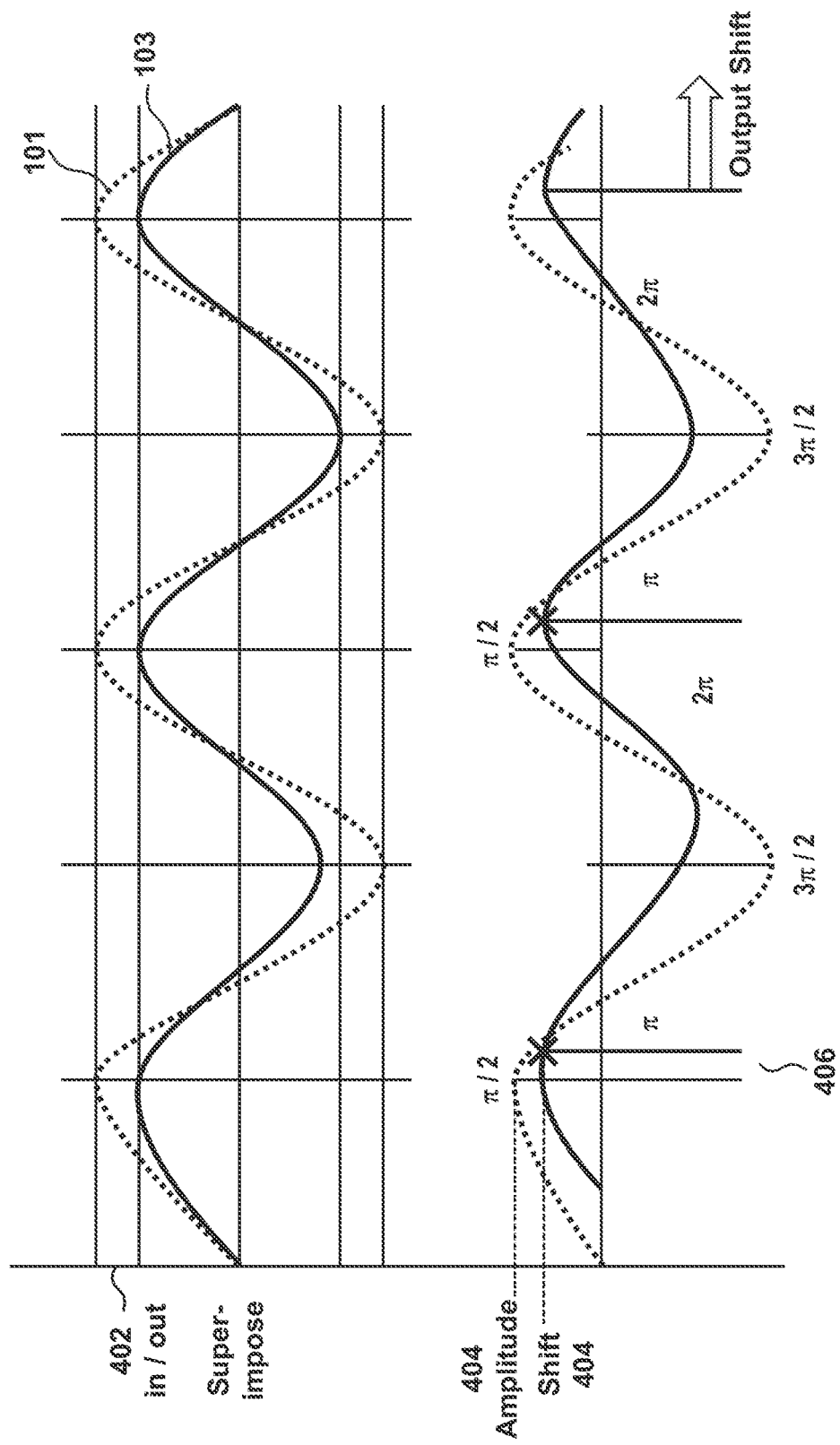
FIG. 4 is a schematic representation of a baseline signal and reflected signal in accordance with one or more implementations.

Referring now to FIG. 4, FIG. 4 depicts an exemplary baseline signal 101 superimposed over reflected signal 103. As shown in FIG. 4, reflected signal 103 undergoes an output shift 402 corresponding to a phase shift 406 and amplitude shift 404. Utilizing the detected amplitude shift and phase shift of the reflected signal and based on the particular portion of the human body corresponding to the location of probe device 110, the phase to amplitude shift is compared to a database of known values for the corresponding portion of the human body under analysis. In the human body structure, general health at the cellular level may be defined in EMF as eV. A hierarchical structure, discussed in further detail below, applies to cells, organs, systems, and the body. By way of sending of the EMF and observing the received pattern (i.e. reflected signal 103) a physical condition of the human body may be determined.

For example, amplitude 404 may be measured in all data, be it of any criteria of the human body. The eV of a specific cell would be changed based on the cell properties. Each cell property has a set frequency at which it can have resonance. Thus, a database of electronic resources 130 (FIG. 1) may store conditions of the human body, which may include data corresponding to individual cells of the human body with respect to resonance frequencies of normal and abnormal cellular structures. This data may be obtained through empirical testing utilizing known physical conditions of the human body as references to establish normal and abnormal value ranges.

In some implementations, in the case of voltage potential differences across cells of the human body, an emitted baseline signal 101 undergoes an amplitude modulation, which can be detected in a reflected signal 103. As shown in FIG. 4, when potential differences across cells of the human body are measured and calculated to provide a value the values may give different results even if there are several rounds of tests done over a gap of time, as depicted by 402 due to a noise element that may distort the complete diagnosis. To avoid this, an algorithm is put in place as soon as the amplitude modulation comes as shown in FIG. 4 (i.e. depicting amplitude 404 to phase shift 406).

Figure 5:
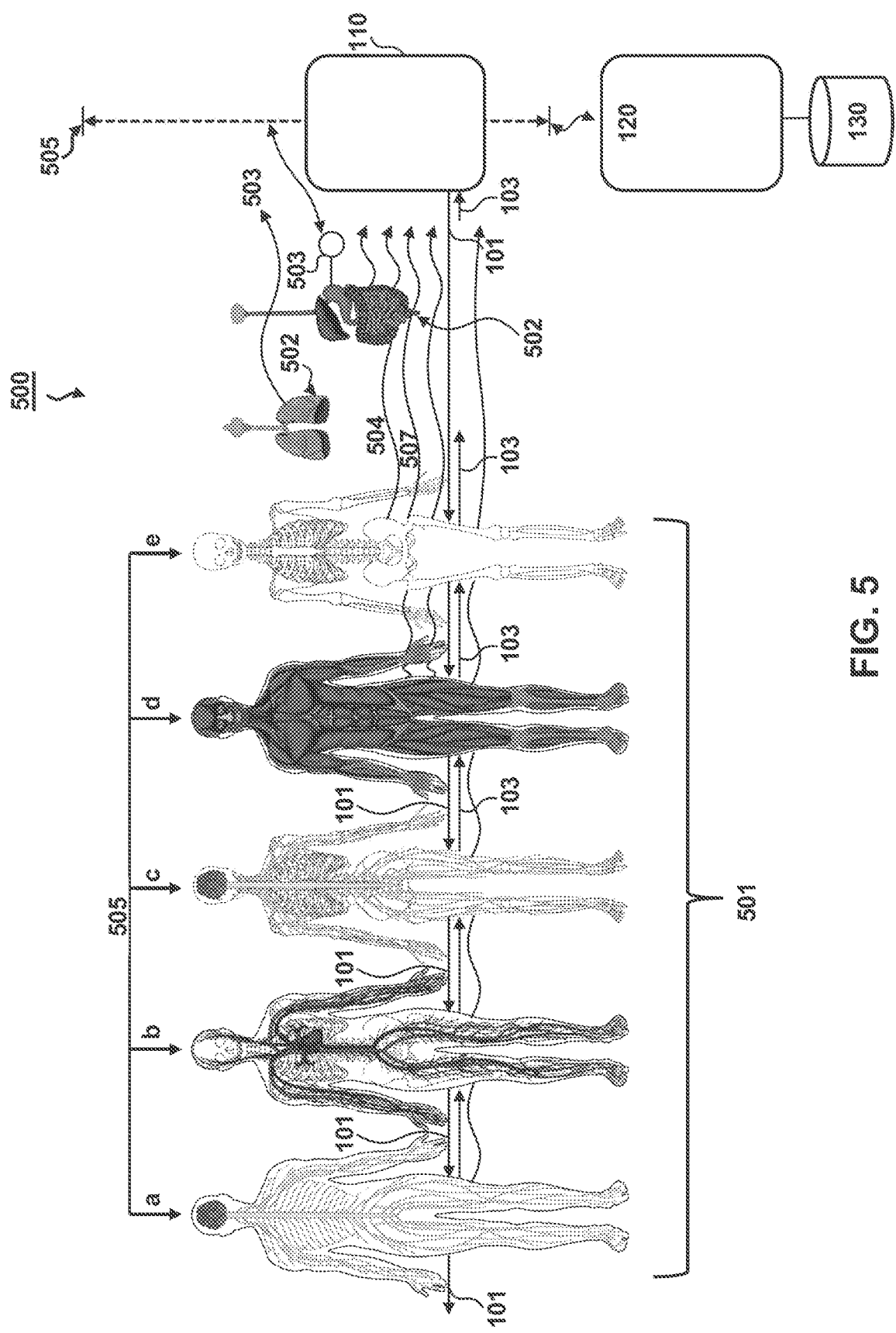
FIG. 5 is a schematic representation of a system for diagnostic analysis system in accordance with one or more implementations.

Referring now to FIG. 5, in conjunction with FIGS. 1-5. FIG. 5 depicts a schematic representation of a diagnostic system 500, which is an exemplary implementation of diagnostic analysis system 100, in which similarly labeled parts and numbers correspond to similar functionality. Diagnostic system 500 may include probe device 110 in communication with processors 120. As shown, probe device 110 may be implemented by scanning probe device 110 over a human body 501.

In some embodiments, probe device 110 may include signal generator (e.g. 118 shown in FIG. 1) and may generate, by the signal generator, a baseline signal. System 500 may emit, by the emitter 112 (shown in FIG. 1), the baseline signal through one or more cells 503 of the human body over a plurality of scanning points 505 (a, b, c, d, e) for a predetermined amount of time. In some embodiments, the predetermined amount of time may be about 100 seconds, or less (for example). In some embodiments, the signal may include an identifier which may include FSK and/or PSK of baseline signal 101, as discussed above. The identifier in conjunction with baseline signal 101 may be used to increase the accuracy of detecting magnetic perturbations corresponding caused by cells 503, which is discussed in further detail below.

As shown in FIG. 5, human body 501 may include human body systems 505. Human body systems 505 may include major organ systems (e.g., eleven) in the human body, which include the circulatory, respiratory, digestive, excretory, nervous and endocrine, immune, integumentary, skeletal, muscle and reproductive systems for example. For simplicity, FIG. 5 illustrates lymphatic immune system 505a, circulatory system 505b, respiratory system 505c, musculature system 505d, skeletal system 505e and organs 502. As shown in FIG. 5, organs 502 include human body cells 503. While FIG. 5 depicts a single cell 503, exemplary implementations described herein utilize probe device 110 to detect a plurality of cells 503 throughout the entirety of human body 501. Detecting human body cells 103 may include detecting chemical and chemically bonded structures (e.g. electrolytes, RNA, DNA, and the like, not shown in FIG. 5), via magnetic perturbations by said cells and cell structures. Discussed in further detail below, each human body cell 503 of human body 501 may emit a resonant frequency 504. The aggregate of the frequencies throughout all cells 503 all correspondence body systems 505 generate electromagnetic (EM) pulses and correspond to EM fields as shown in FIG. 5.

For example, as human body 501 is the aggregate of all cells 503, which are in a continuous cycle of growth, physical conditions of the human body may be observed by analyzing the electromagnetic pulses and fields 507 generated by the aggregate of all cells 503. By emitting an electromagnetic wave (e.g., signal 101) with dynamic frequency ranging near 14 GHz or more (for example), probe device 110 may excite cells 503 when a frequency range of signal 101 corresponds to a resonating frequency of cells 503 and/or cell structures. For example, cells 503 and structures within cells 503 (e.g. RNA, DNA and the like, not shown) may emit EM pulses 507 at specific resonance frequencies that interact, via constructive wave properties, with particular frequencies of baseline signal 101.

Due to constructive and deconstructive wave properties of EM wave propagation, EM field and impulses 507 may interact with reflected signals 103. As reflected signal 103 have propagated through all cells 503 and human body systems 505, as shown in FIG. 5, magnetic perturbations caused by cells 503 can be observed. For example, electromagnetic pulses 507 emitted by cells 503 and corresponding magnetic perturbations caused by interaction of pulses 507 with reflected signal 507 provide observations of the physical condition of cells and/or the human body. In this manner observations of the physical condition of the human body may be quantized and deduced by comparison of empirical data derived from known conditions of cells and/or the human body.

Cells 503 of human body 501 include development, differentiation, regeneration, and apoptosis with other cells 503 and are constantly renewing through cellular division. For example, cells 503 may include blood cells of circulatory system 505b. Blood cells 503 may renew at a rate of about 100 million per minute, for example. During the process of cellular division and growth, the electrically charged bodies of atomic nuclei (not shown), which constitute the basic unit of cell 503, and the electrons outside the nucleus, are in a constant state of high-speed movement and flux. An accelerating electrically charged particle (e.g. an electron) emits electromagnetic pulses of particular frequency waves (e.g., a resonance frequency of the particular cell).

As shown in FIG. 5, electromagnetic wave signals 504 of cells 503 are emitted by each and every human cell within all system 505 throughout human body 501. Diagnostic analysis system 500 may receive, by the receiver 114 (FIG. 1), one or more reflected signals that have propagated through the one or more cells 503 of the human body 501. The emitted electromagnetic wave signals 504, 507 of cells 503 and human body system 505 vary under different conditions such as normal, sub-clinical (e.g. prediabetic), or diseased, for example. Thus, when these specific electromagnetic wave signals 504, 507 are evaluated via reflected signal 103, signals 504, 507 can be measured and can determine the numerous values seen in any given diagnostic analysis of the human body for both normal values and abnormal values, for example, values of results may correspond to RBC, Bone density, Testosterone, and the like.

For example, evaluation of signals 103, 504, 507 may, in some implementations, be implemented determining, utilizing processors 120, a power spectral density (PSD) of the reflected baseline signal 103. Processors 120 may determine a spectral variance in the PSD of the reflected baseline signal 103 relative to baseline signal 101. In doing so magnetic perturbations caused by abnormal cells can be observed and identified. In some implementations, baseline signal 101 includes identifier, which may be utilized for further signal identification purpose.

In some implementations, diagnostic analysis system 100, 500 may compare, by the one or more processors, the spectral variance to one or more predetermined spectral variances corresponding to one or more conditions of the human body. Predetermined spectral variances corresponding to one or conditions of the human body have been empirically deduced through copious testing and research. For example, by way of empirical research and testing, external resources 130 may include a database corresponding to conditions of the human body and known spectral variances corresponding to such conditions. For example, abnormal values for signal 504 arise when the spin and orbit of electrons outside the atomic nucleus of cell 504 change, thereby causing the change of atoms constituting a change of small biomolecules and large biomolecules, thus changing cell 503 and thus impacting the organ 502.

Because the electron is a charged body, when the spin of electrons outside the atomic nucleus and orbit change, the electromagnetic wave 504, 507 emitted by the atoms that comprise cell 503 and body systems 505 will change. The energy of the electromagnetic wave changes caused by abnormal values (i.e. illness) is substantially meniscal and difficult to detect, occurring at the Micro Gauss or Nano Gauss level. Accordingly, receiver 314 may be configured for detecting magnetic field perturbations corresponding to at least a portion of the reflected signal 103 in an order of magnitude corresponding to one Nano Gauss are smaller. Thus, by comparison of the spectral variances, and specifically the amplitude to phase variances, to the one or more predetermined spectral variances, one or more implementations described herein may determine a condition of the human body, based on the comparison of the spectral variances. For example, conditions of the human body may include conditions typically evaluated using tests such as CMP, urinalysis, glucose testing, a lipid panel, heart rate, heart rate variability, insulin tests, toxicology tests, oxygenation monitoring, and the like.

In some implementations, a frequency and energy of this magnetic field caused by abnormal conditions in cells may be determined by holding probe device 110 over cell 503 for a predetermined amount of time (e.g. 100 seconds). The received data may be compared with the resonance and frequency spectra of a standard cells having known atomic structures and electromagnetic measurement values (e.g., determined through empirical testing). For example, determining the spectral variance in the PSD may include determining amplitude and phase shift of the reflected signal relative to the baseline signal. In some implementations, whether a normal or abnormal value is measured, each frequency spectrum generated that backpropagates to probe device 110 shows the difference in the change in amplitude and in phase. This may be determined by analyzing a power spectrum density (PSD) of the frequency spectrum generated and received back by probe 110, as discussed above.

In some implementations, comparing the baseline signal 101 with reflected signal 103 may include leveling an amplitude and correcting a phase shift. This may provide the value (normal or abnormal) at the cellular level (e.g., cell 503), with this cellular level pattern in turn deducing values at organ 502 and at the systemic level 505 (e.g. systems 505a-e) and any interconnectivity therein. For example, processors 120 (FIG. 1) may be configured to examine any and all chemical, cellular, organ, and/or systemic data points individually, and as a whole, to discern the impact and determine values for diagnostic collection.

In some implementations, a quantum of normal and abnormal values sensed and "collected" by probe device 110 are processed by processors 120 implementing a multi-algorithmic system. For example, in some implementations, amplitude and phase data of modulated signals may be input into multiple and analyzed on multiple layers. System 100 may probe and analyze areas that are common to multiple body/organ systems and independently expose each system and create an output where several specialists may be involved. Positive quantum values indicate normal body conditions, and negative quantum values indicate abnormal body conditions. The size of the quantum value indicates the value or intensity of the normal or abnormal conditions. For example, conditions of the body may include viscosity of blood, and tensile strength of blood vessels and heart chambers itself, heart rate, heart rate variability, and the like.

In some implementations, cells 503 may include cancer cells, for example. Cancer cells' atomic structure may differ from normal healthy cells, and the electromagnetic waves emitted by cancer cells also differ from the electromagnetic waves emitted from normal cells. Based on the baseline resonance spectra, which has been previously determined through empirical testing and stored in electronic resources 130, for example, when there are cancer cells present in body 501 abnormal resonance will occur and probe device 110 and/or processors 120 will detect the abnormal signal emitted by cancer cells. The greater the number of cancer cells the more intense the abnormal signal will be (e.g., the quantum value of the abnormal signal will be more negative). If there are no cancer cells, resonance outside of baseline frequencies will not occur, and the quantum value will tend to be positive. In some implementations results are viewed by clinicians for a recommendation of next steps (e.g., treatment, additional tests, etc.).

In some implementations diagnostic analysis is the 500 may examine all cellular structures and compartments of all cells in human body 501. For example, in some implementations diagnostic analysis system 500 may examine all 79 organs of the human body 501 and all 11 systems of the human body (e.g., Circulatory, Digestive, Endocrine, Integumentary/Exocrine, Lymphatic/Immune, Muscular, Nervous, Excretory (Renal and Urinary), Reproductive, Respiratory, and Skeletal). In some implementations, processors 120 (FIG. 1) may implement interconnectivity diagnostic analysis wherein system 100 examines any and all chemical, cellular, organ, and/or systemic data points individually and as a whole to discern the impact and determine values for diagnostic collection to abnormal (e.g. a value range from normal to abnormal for ALP).

As discussed above, in some implementations, server processors 120 may include interconnectivity functionality that examiners any and all chemical, cellular, organ, and/or systemic data points individually and as a whole to discern the impact and determine values for diagnostic collection. In some implementations, upon determining that there are abnormal conditions of the human body based on comparison of spectral variances, diagnostic analysis system 500 may transmit a report indicating the detected conditions of the human body to a clinician and/or other users.

Figure 6:
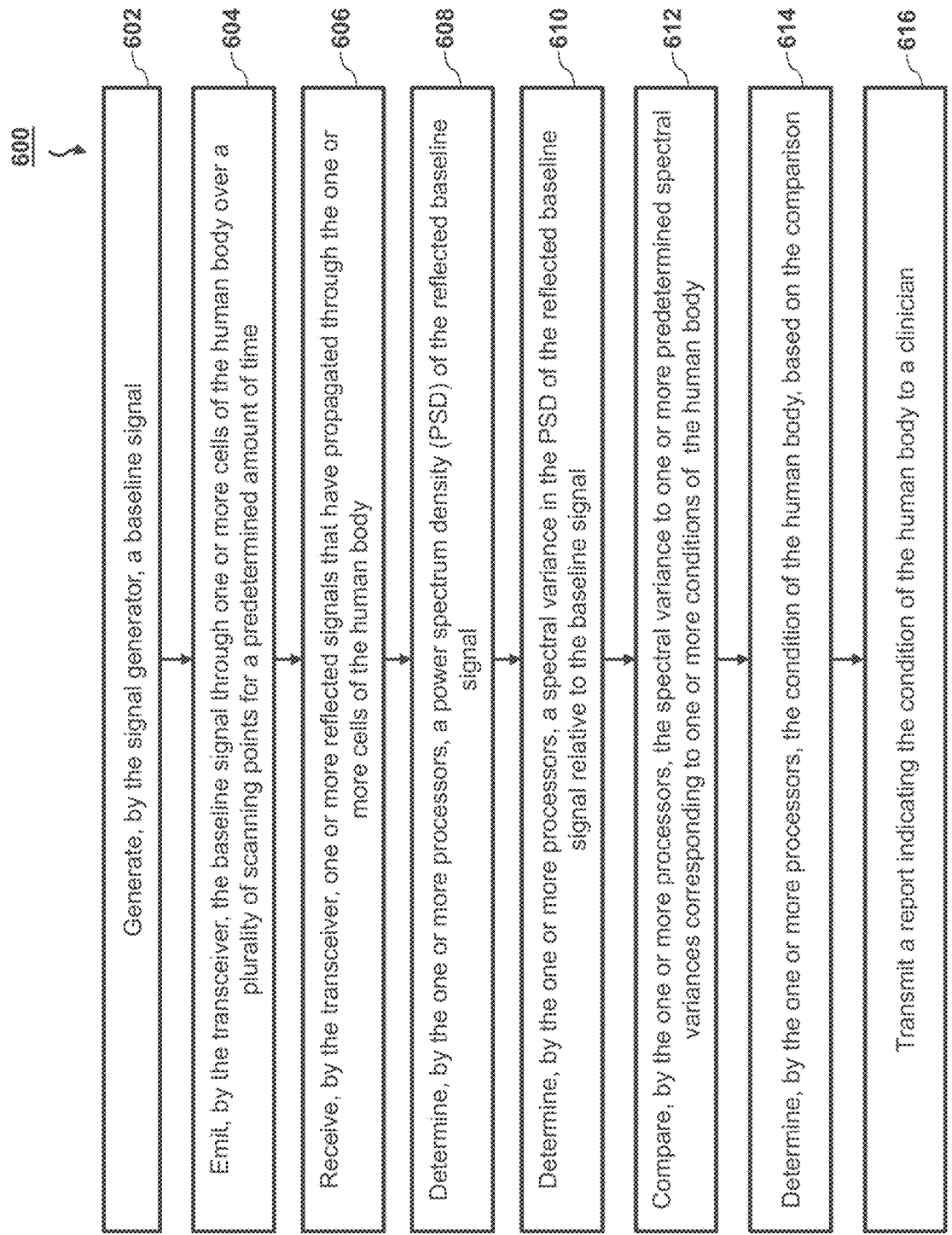
FIG. 6 depicts a method for diagnostic analysis in accordance with one or more implementations.

Referring now to FIG. 6, FIG. 6 depicts a method in accordance with one or more implementations described herein. The operations of method 600 presented below are intended to be illustrative. In some implementations, method 600 may be accomplished with one or more additional operations not described, and/or without one or more of the operations. Additionally, the order in which the operations of method 600 are illustrated in FIG. 6 and described below is not intended to be limiting.

As shown in FIG. 6, at an operation 602, a baseline signal is generated by the signal generator. Operation 602 is performed by a signal generator the same or similar to signal generator 118 of FIG. 1.

At an operation 604, the baseline signal may be emitted through one or more cells of the human body over a plurality of scanning points for a predetermined amount of time. Operation 604 is performed by an emitter the same or similar to emitter 112 of FIG. 1.

At an operation 606, one or more reflected signals that have propagated through the one or more cells of the human body may be received. Operation 606 is performed by a receiver the same or similar to receiver 114 of FIG. 1.

At an operation 608, a power spectrum density (PSD) of the reflected baseline signal may be determined. Operation 608 is performed by processors the same or similar to server processors 120 of FIG. 1

At an operation 610, a spectral variance in the PSD of the reflected baseline signal relative to the baseline signal may be determined. Operation 610 is performed by processors the same or similar to server processors 120 of FIG. 1.

At an operation 612, the spectral variance may be compared to one or more predetermined spectral variances corresponding to one or more conditions of the human body. Operation 612 is performed by processors the same or similar to server processors 120 of FIG. 1

At an operation 614, one or more conditions of the human body may be determined, based on the comparison. Operation 614 is performed by processors the same or similar to server processors 120 of FIG. 1.

At an operation 616, a report indicating the condition of the human body may be transmitted to a clinician and/or other users. Operation 616 is performed by processors the same or similar to server processors 120 of FIG. 1

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred implementations, it is to be understood that such detail is solely for that purpose and that the disclosure is not limited to the expressly disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A system for providing diagnostic analysis of a physical condition of a human body, the system comprising:
   a signal generator;
   an emitter;
   a receiver; and
   one or more processors in communication with a memory having non-transitory computer readable instructions stored thereon, that when executed by the one or more processors cause the system to:
   generate, by the signal generator, a baseline signal;
   emit, by the emitter, the baseline signal through one or more cells of the human body over a plurality of scanning points for a predetermined amount of time;
   receive, by the receiver, one or more reflected signals that have propagated through the one or more cells of the human body, wherein the receiver is configured to detect magnetic field perturbations;
   determine, by the one or more processors, a power spectrum density (PSD) of the reflected baseline signal;
   determine, by the one or more processors, a spectral variance in the PSD of the reflected baseline signal relative to the baseline signal;
   compare, by the one or more processors, the spectral variance to one or more predetermined spectral variances corresponding to one or more physical conditions of the human body;
   determine, by the one or more processors and based on the comparison, the physical condition of the human body, wherein the determined physical condition is determinable based on biological conditions of the human body; and
   transmit a report indicating the physical condition of the human body.

2. The system of claim 1, wherein determining the spectral variance in the PSD comprises determining an amplitude and phase shift of the reflected signal relative to the baseline signal.

3. The system of claim 1, wherein the signal generator, the emitter, and the receiver comprise a wireless handheld device.

4. The system of claim 1, wherein the emitter and the receiver are coupled to a dielectric.

5. The system of claim 1, wherein the signal generator comprises a dual phase lock loop (PLL) clock generator having an operating range of at least 14 GHz.

6. The system of claim 1, wherein the predetermined amount of time is no more than 100 seconds.

7. The system of claim 1, wherein the baseline signal comprises a first carrier signal corresponding to a primary baseline signal and a second carrier signal corresponding to an identifier.

8. The system of claim 7, wherein the identifier comprises a frequency shift key (FSK) and phase shift key (PSK) of the baseline signal.

9. The system of claim 1, wherein the plurality of scanning points comprises at least 2 billion data points.

10. The system of claim 1, wherein the magnetic field perturbations correspond to at least a portion of the reflected signal in an order of magnitude corresponding to one Nano Gauss or smaller.

11. The system of claim 1, wherein the one or more processors comprise a remote computing device having a display.

12. The system of claim 1, wherein transmitting the report comprises rendering on the display at least one of: an indication of the PSD of the reflected baselines, an indication of the spectral variance, or an indication of the determined physical condition of the human body on the display.

13. A method for providing diagnostic analysis of a physical condition of a human body utilizing a system comprising: a signal generator, an emitter, a receiver, and one or more processors in communication with a memory having non-transitory computer readable instructions stored thereon, that when executed by the one or more processors cause the system to execute the method, the method comprising:
    generating, by the signal generator, a baseline signal;
    emitting, by the emitter, the baseline signal through one or more cells of the human body over a plurality of scanning points for a predetermined amount of time;
    receiving, by the receiver, one or more reflected signals that have propagated through the one or more cells of the human body, wherein the receiver is configured to detect magnetic field perturbations;
    determining, by the one or more processors, a power spectrum density (PSD) of the reflected baseline signal;
    determining, by the one or more processors, a spectral variance in the PSD of the reflected baseline signal relative to the baseline signal;
    comparing, by the one or more processors, the spectral variance to one or more predetermined spectral variances corresponding to one or more physical conditions of the human body;
    determining, by the one or more processors and based on the comparison, the physical condition of the human body, wherein the determined physical condition is determinable based on biological conditions of the human body; and
    transmitting a report indicating the physical condition of the human body.

14. The method of claim 13, wherein determining the spectral variance in the PSD comprises determining an amplitude and phase shift of the reflected signal relative to the baseline signal.

15. The method of claim 13, wherein the signal generator, the emitter, and the receiver comprise a wireless handheld device.

16. The method of claim 13, wherein the emitter and the receiver are coupled to a dielectric.

17. The method of claim 13, wherein the signal generator comprises a dual phase lock loop (PLL) clock generator having an operating range of at least 14 GHz.

18. The method of claim 13, wherein the predetermined amount of time is no more than 100 seconds.

19. The method of claim 13, wherein the baseline signal comprises a first carrier signal corresponding to the baseline signal and a second carrier signal corresponding to an identifier.

20. The method of claim 19, wherein the identifier comprises a frequency shift key (FSK) and phase shift key (PSK) of the baseline signal.

21. The method of claim 13, wherein the plurality of scanning points comprises at least 2 billion data points.

22. The method of claim 13, wherein the magnetic field perturbations correspond to at least a portion of the reflected signal in an order of magnitude corresponding to one Nano Gauss or smaller.

23. The method of claim 13, wherein the one or more processors comprise a remote computing device having a display.

24. The method of claim 13, wherein transmitting the report comprises rendering on the display at least one of: an indication of the PSD of the reflected baselines, an indication of the spectral variance, or an indication of the determined physical condition of the human body on the display.

* * * * *